United States Patent
Stecker et al.

(10) Patent No.: US 6,915,166 B1
(45) Date of Patent: Jul. 5, 2005

(54) OPTIMIZING COCHLEAR IMPLANT ELECTRODE SELECTION

(75) Inventors: Mathias Stecker, Soelden (DE); Ernst Ludwig Von Wallenberg, Muelheim (DE); Norbert Dillier, Kusnacht (CH); Wai Kong Lai, Zurich (CH); Jochen Nicolai, Basel (CH); Roland Laszig, Umkirch (DE); Joachim Mueller-Delle, Kiel (DE); Denise Cafarelli-Dees, West Mein Near Petersfield (DE)

(73) Assignee: Cochlear Limited, Lane Cove (AU)

( * ) Notice: Subject to any disclaimer, the term of this patent is extended or adjusted under 35 U.S.C. 154(b) by 399 days.

(21) Appl. No.: 10/009,044

(22) PCT Filed: Aug. 28, 2000

(86) PCT No.: PCT/AU00/01019

§ 371 (c)(1),
(2), (4) Date: Apr. 30, 2002

(87) PCT Pub. No.: WO01/15773

PCT Pub. Date: Mar. 8, 2001

(30) Foreign Application Priority Data

Aug. 27, 1999  (AU) .............................................. PQ2499

(51) Int. Cl.[7] .............................. A61N 1/36; A61N 1/18; H04R 25/00
(52) U.S. Cl. ............................... 607/55; 607/45; 607/56
(58) Field of Search .............................. 607/45, 55–57; 600/25; 623/10

(56) References Cited

U.S. PATENT DOCUMENTS 5,609,616 A   3/1997  Schulman et al. ............. 607/56
6,415,185 B1 * 7/2002  Maltan ......................... 607/57

FOREIGN PATENT DOCUMENTS

| EP | 0624383 A1 | 5/1993 | ............ A61N/1/00 |
| WO | WO 94/14376 A1 | 7/1994 | ............ A61B/5/12 |
| WO | WO 97/09863 A1 | 3/1997 | ............ A61B/5/12 |
| WO | WO 97/48447 A1 | 12/1997 | ............ A61N/1/36 |

OTHER PUBLICATIONS

Summary of Result Using the Nucleus C124M Implant to Record the Electrically Evoked Compound Action Potential; Ear & Hearing (The Official Journal of the American Auditory Society); Feb. 1999; vol. 20, No 1; pp. 45–59; by Paul J Abbas et al.

PCT International Search Report dated Sep. 20, 2000 for PCT/AU00/01019 (WO 01/15773 A1); international publication date Mar. 8, 2001; international filing Aug. 28, 2000; Inventors: Stecker. Mathias et al.

* cited by examiner

Primary Examiner—Carl Layno
(74) Attorney, Agent, or Firm—Jagtiani+Guttag

(57) ABSTRACT

A method is described to allow for better selection of electrodes for neural stimulation, for example in a cochlear implant. A series of stimuli, at different stimulation levels, are provided at each electrode to be tested, and the neural response to each stimulus is measured, using an implanted electrode. A value is then calculated relating stimulus level to response, to allow the relative responsiveness of electrodes to be determined. This can then be used as the basis for a stimulation map used to select which electrodes are stimulated and at what level.

9 Claims, 7 Drawing Sheets

☐ "steep" electrode   ▨ "shallow" electrode   ☐ active electrodes are framed

OPTIMIZING COCHLEAR IMPLANT ELECTRODE SELECTION

TECHNICAL FIELD

The present invention relates to methods for optimising the selection of electrodes for stimulation in neural stimulation devices such as cochlear implants, and devices utilising such methods.

BACKGROUND ART

Post-implantation, recipients of intracochlear implants exhibit considerable variation in speech perception performance. Such variability may have many reasons —one explanation is a non-homogeneous spatial distribution of residual VIII$^{th}$ nerve fibers or of the interface between nerve fibers and electrodes. When comparing different stimulation sites within the cochlear during speech processor fitting, patients sometimes report differences in sound quality. Deactivation of those electrodes with minor quality or distorted sound perception often improves general sound sensation and speech understanding. Furthermore it has been reported that selecting different electrode groups for Continuous Interleaved Sampling (CIS) stimulation has significant influence on speech perception in a number of subjects (Wilson B S, Finley C C, Lawson D T, et al. Design and evaluation of a continuous interleaved sampling (CIS) processing strategy for multichannel cochlear implants. J Rehabil Res Dev 1993; 30:110–116.)

At present, the process for selecting which electrodes should be utilised requires eliciting comments from the patient as to whether or not the benefit of the prosthesis is improved or decreased upon making an adjustment to the electrodes being used for stimulation. There are a number of problems associated with this prior art approach. For example the adjustment is not made according to any quantitative parameter but rather is based on the somewhat subjective judgements/reactions of the patient Furthermore some patients, for example young children, may not be able to readily indicate an improvement or decrease in the quality of their hearing perception during the adjustment process. Yet a further problem is that the present approach does not readily lend itself to automation, relying as it does on trial and error, and the conscious feedback of the patient.

It is an object of the present invention to provide a method, capable of automatic operation, for selecting good and poor electrodes and for utilising this information to select electrodes for stimulation.

SUMMARY OF THE INVENTION

In a broad form, the present invention provides a method for determining which electrodes in a multi-electrode neural stimulator device are working well or poorly, by conducting a series of tests on each electrode and measuring the evoked response to the stimulation, for various levels of stimulation and for each electrode of interest, and calculating a value relating stimulus level to response level for each electrode.

In one aspect the present invention provides a method for determining the relative responsiveness of electrodes in an implanted multi-electrode intracochlear prosthesis, including the steps of (a) measuring the amplitude of the evoked response to a set of stimuli at different stimulation levels for one of the electrodes in said prosthesis;

(b) calculating a value relating the evoked responses to the stimulus levels for each electrode;

(c) repeating steps (a) and (b) for each electrode for which data is required; and (d) determining the relative responsiveness of the electrodes by comparing the values of step (b) for the tested electrodes. Preferably, step (b) is performed by deriving the slope of the best fit regression line on a plot of stimulus level against peak to peak amplitude of evoked response. However, other derived values may be used, for example some other parameter of the evoked response, or the simple value of the peak to peak amplitude. The invention also contemplates using combinations of stimulating electrodes to determine which combination is most effective.

In a preferred use of the data on responsiveness, consideration is given also to the spectral distribution of the electrodes. For example, the steepest slopes may be clustered in a particular frequency range, so that to select only these electrodes will produce an unbalanced distribution of electrodes for distribution. It is preferred to balance the selection of electrodes only on responsiveness with selection so as to provide a more even distribution of stimulation sites.

The values from the method can then be used to determine which electrodes, for example, are performing most poorly and exclude these from a stimulation strategy map. More sophisticated uses of this information are of course possible —prior to the present invention, no such data had been utilised to objectively measure electrode performance.

It is considered that stimulation sites with a steeper growth function contribute more to speech perception performance than stimulation sites with shallower growth function, and that the specific electrode selection based on telemetry measurements will improve speech-coding performance. The present invention provides a way to improve speech processor fitting by using predominantly those stimulation sites with a relatively steep electrically evoked compound action potential (ECAP) amplitude growth function.

There are several reasons why the slope of the amplitude growth function has been chosen as a stimulation site assessment tool. In clinical practice, a large variability in the slope of the ECAP amplitude growth function has been found. This variability has been observed both within subject (over the electrode array) as well as between subjects.

In comparison to other response parameters such as amplitude, latency or dynamic range, the slope of the amplitude growth function is a more robust parameter because it is based on statistical regression calculation. It is postulated that with increasing stimulus level, the number of responding nerve cells —and thus the amplitude of the neural response —will grow faster if the stimulation site is located in an area of high ganglion cell density, compared to an area with low spiral ganglion density.

The present invention also includes a device adapted to perform the method as described.

BRIEF DESCRIPTION OF THE DRAWINGS

One implementation of the present invention will now be described in more detail with respect to the accompanying figures, in which.

DETAILED DESCRIPTION OF THE INVENTION

Figure 1:
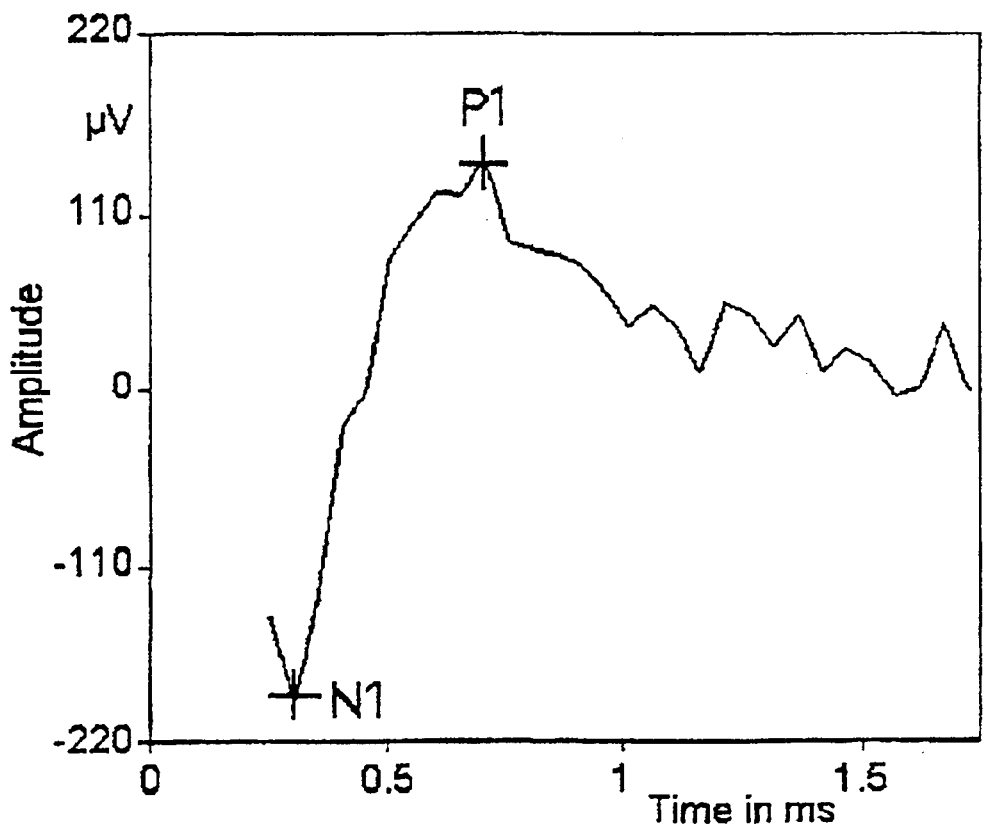
FIG. 1 is a graph showing an example of a recorded ECAP using NRT ™.

It will be appreciated that the present invention may be implemented utilising any suitable cochlear implant and speech processor. It is highly desirable that a telemetry system be provided as part of the implant system, to facilitate the ready acquisition of the evoked neural response data discussed. It will be appreciated that alternative measures of neural response could equally be utilised to implement the present invention. The invention could also be applied to other neural stimulation situations.

The example discussed below utilises Neural Response Telemetry™(NRT™) as implemented in the Nucleus ® N24 CI-system (Abbas P J, Brown C J, Shallop J K, et al. Summary of results using the Nucleus CI24M Implant to record the electrically evoked compound action potential. Ear & Hearing 1999; 20:45–59; Stypulkowski P H, van den Honert C, Kvistad S D. Electrophysiologic evaluation of the cochlear implant patient. Otolaryngol Clin North Am 1986; 19:249–257).

This technique has at least two advantages over conventional Electrical Evoked Auditory Brainstem Responses (EABR): there is no need for surface electrodes, sedation or additional averaging equipment, and it can deliver direct site specific information about the spatial distribution of neural activity.

To assess and categorize the 22 intracochlear electrodes as either "poor" or "good", this specific technique uses a measurement of the slope of the amplitude growth function of the Compound Action Potential (CAP).

EXAMPLE

The following example illustrates how the technique of the present invention can be implemented in real patent situations.

Two German speaking patients with more than one year CI-experience and good performance were recruited for this study. Subject profiles are summarized In the following table.

| Subject Profiles | | |
|---|---|---|
| Subject initials | WW | EK |
| Gender | male | female |
| Age (years) | 72 | 38 |
| Aetiology | progressive | progressive |

Both subjects use the body worn SPrint™ speech processor, and were tuned up with SPEAK™ speech processing strategy. Six months prior to this experiment, both were converted to ACE™ speech processing strategy. Previous to the study described here, the subjects had not been exposed to a CIS coding strategy.

NRT™ measurements were recorded using electrodes 20 to one as the stimulating electrode pair, with the recording electrode spaced two electrodes apart, apically from the stimulation site. The NRT™-software version 2.04 developed at the ENT Department of the University Hospital Zurich was used. The standard parameter settings being as follows:

NRT™ stimulation and recording parameters for both subjects

| NRT ™ stimulation and recording parameters for both subjects | |
|---|---|
| Stim. Electrode No.: | 1 . . . 20 |
| Rec. electrode No.: | 3 . . . 22 |
| Stim. mode: | MP1 |
| Rec. mode: | MP2 |
| Pulse rate: | 80 pps |
| Rec. window | 1.6 ms |
| Delay | WW: 74 µs, EK: 47 µs |
| No. of averages: | WW: 100, EK: 200 |
| Pulse width: | 25 µs/phase |
| Masker advance: | 50 µs |
| Masker level: | WW: probe level + 5 CL; EK: fix at LAPL |

The delay is measured from the end of the probe stimulus to the start of the recording.

Gain and delay of the recording system were optimized for the subjects (individually). The parameters were held constant for all measured electrodes.

Beginning at the loudest acceptable level (LAPL), a series of up to nine recordings were made with stimulation levels at 5 CL intervals in descending order.

Figure 2:
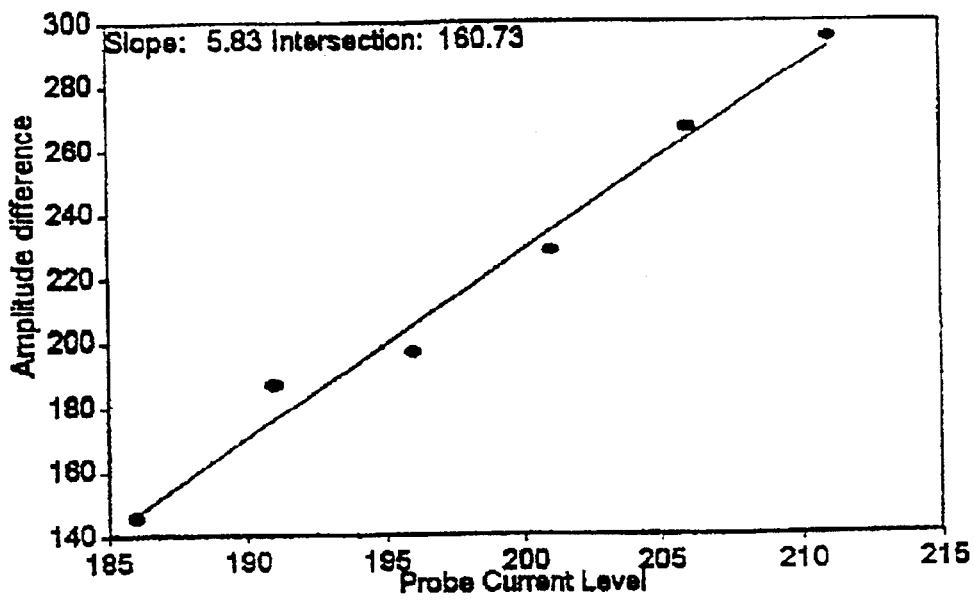
FIG. 2 is a graph showing the amplitude growth function for an electrode.

For each recording, the peak to peak amplitudes were determined and linear regression lines were calculated to estimate the slope of the corresponding amplitude growth functions (FIGS. 1 and 2). If necessary, prior to calculation of the regression function, outliers were excluded to maximize the correlation coefficient. However, each calculated slope is based on a minimum of four points. Most of the outliers excluded were either measured within the noise floor, showed a saturation effect at high stimulation levels or the amplitude of these recordings could not be reliably measured because N1 had too short a latency to be captured.

The estimated amplitude growth slopes were plotted over the stimulation sites separately for each subject and divided in two groups, using the median value as the divider. Stimulation sites with an amplitude growth slope above the median value formed the group of "steep stimulation sites", those showing a slope below the median were labelled "shallow stimulation sites".

For subject WW, two 9-channel CIS maps, one using predominantly "steep" stimulation sites and one using predominantly "shallow" stimulation sites were generated. When selecting the stimulation sites, clustering of active stimulation sites was avoided. Instead, "steep" and "shallow" sites across the entire length of the electrode array were used. The result was termed a "steep mix" CIS (using mainly "steep" stimulation sites) and a "shallow mix" CIS (using mainly "shallow" stimulation sites). The stimulation rate used for both CIS maps was 1200 pps —the same rate as used in the subject's previous ACE™ maps.

For subject EK, the electrode array from electrode 20 to 1 was divided into four consecutive segments of five electrodes each. The stimulation site of each segment showing the steepest amplitude growth function was selected for a "steep" 4-channel CIS map, while the site with the shallowest growth function in each segment was selected for a "shallow" 4-channel CIS map. Because EK's previous ACE™ map used 1800 pps stimulation rate, the two 4-channel CIS maps were programmed using this same stimulation rate. In addition to the two CIS maps, a modified ACE™ map was also tested. The only difference to the subject's previous ACE™ map was that the four stimulation sites showing the shallowest amplitude growth function were deactivated.

Prior to speech comprehension testing, the subjects were given a few minutes familiarization with the new maps. For WW, Göttingen Sentences in noise presented at 70 dB SPL with +10 dB S/N were used. For EK, Freiburg Numbers in noise, presented at 70 dB SPL with 0 dB S/N and Freiburg Monosyllabic Words presented at 70 dB SPL in quiet were used.

Figure 3:
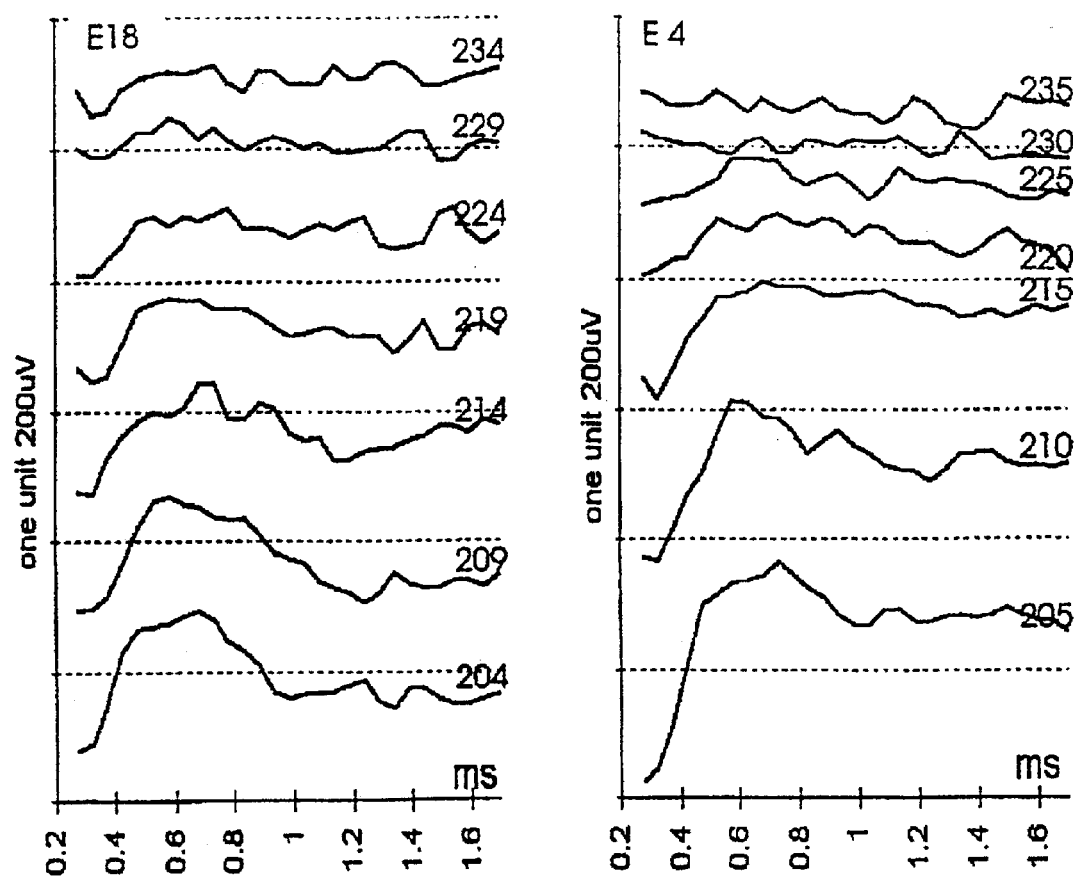
FIG. 3 shows ECAPs from subject WW for electrodes 4 and 18.

With both patients, ECAP amplitude growth functions could be calculated on all 20 measured electrodes. FIG. 3 shows two measurement series from patient WW. On electrode four, the ECAP showed a relatively steep amplitude growth and a high threshold. In contrast, the neural response on electrode 18 has a relatively shallow growth function and a relatively low threshold.

Compared to other NRT™ parameters such as the response threshold or maximum amplitude, the slope of the amplitude growth function showed the largest variability along the electrode array. For WW the minimum slope was 4.8 $\mu$V/CL, the maximum 14.9 $\mu$V/CL. The mean was 10.5 $\mu$V/CL, the median 10.4 $\mu$V/CL. For EK the minimum amplitude growth slope was 4.2 $\mu$V/CL, the maximum 13.5 $\mu$V/CL. The mean was 7.0 $\mu$V/CL and the median 6.6 $\mu$V/CL.

Figure 4:
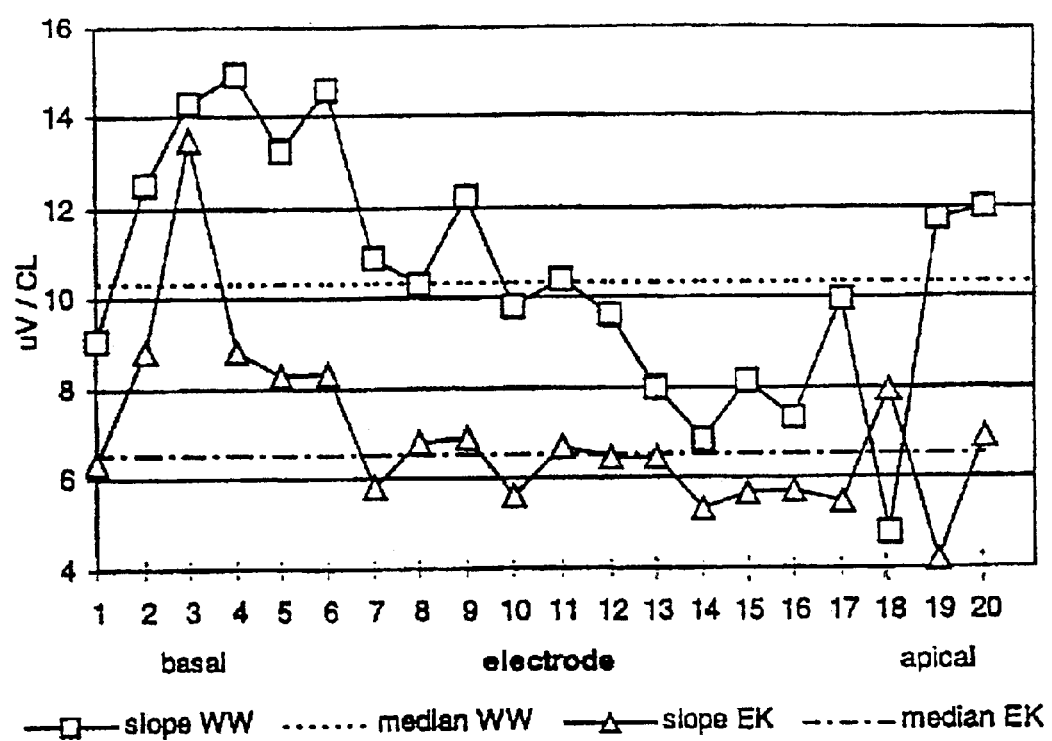
FIG. 4 is a graph of ECAP amplitude growth functions against stimulating electrode.

The distribution of the slope values along the electrode array is shown in FIG. 4. Subject WW has a steep amplitude growth in the basal part of the cochlear. Towards the apical end a monotonously decreasing slope was measured. With subject EK, particularly across the medial to apical part of the electrode array, the slope of the ECAP amplitude growth function seems to be more uniform.

Figure 5:
FIG. 5 shows schematically the steep and shallow electrodes as selected in the example.
Figure 5:
Figure 5:
Figure 5:
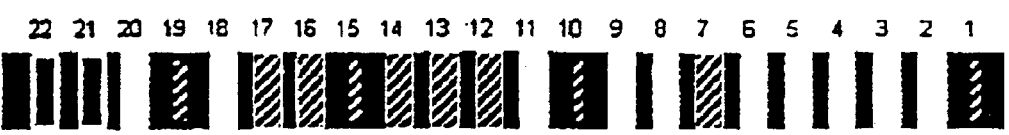

According to the methods described previously, two alternative CIS maps for each subject were created: a "steep" map and a "shallow" map. FIG. 5 shows the spatial distribution of the selected electrodes of each map.

Both subjects were surprised by the different sound quality compared to their familiar ACE™ map. All CIS maps sounded significantly higher in pitch compared to ACE™.

Without knowing which of the two CIS maps was presented, subject WW spontaneously preferred the "steep" 9-channel CIS map compared to the "shallow" 9-channel CIS map. The "shallow" map was described as "muffled", "distorted" and "metallic".

Subject EK did not accept the quality of any of the 4-channel CIS maps, reporting the sound as "extremely metallic" and "distorted". With the modified ACE™ map excluding the four shallowest stimulation sites (19, 17, 14, 10) EK noted a "slightly sharper sound", compared with the familiar ACE™ map.

Figure 6:
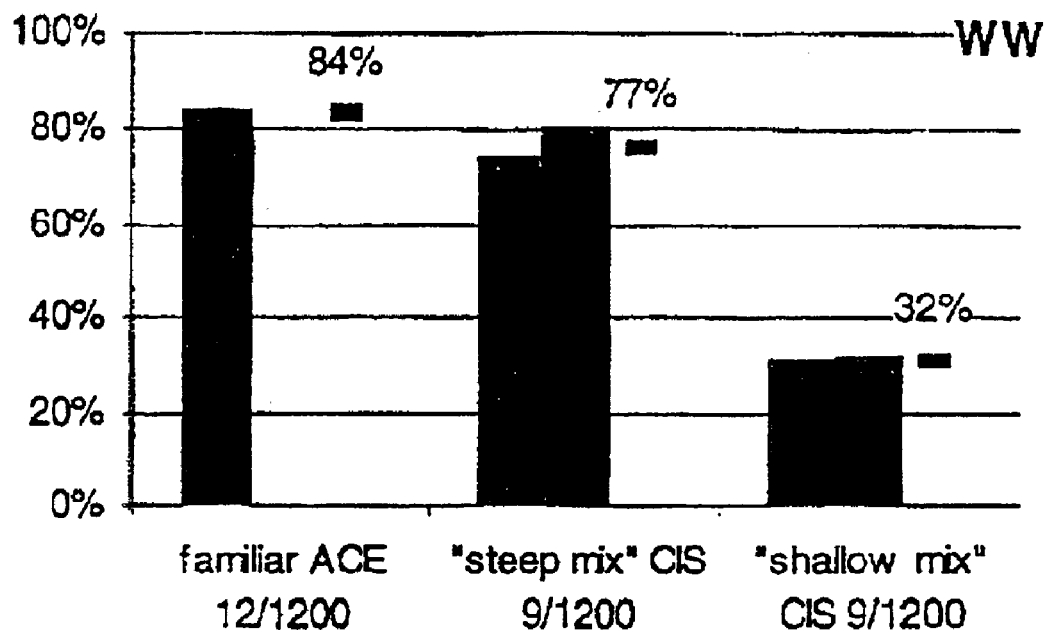
FIG. 6 is a graph showing the results of speech comprehension tests.
Figure 6:
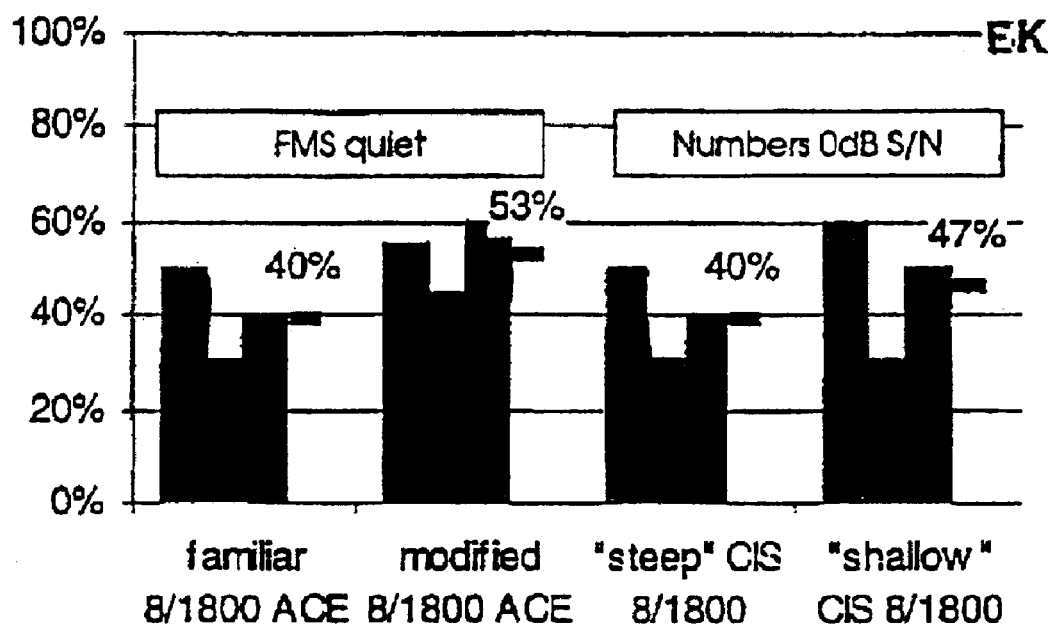

These subjective impressions correspond to the results of the speech comprehension tests performed during the same session (FIG. 6).

Subject WW showed better performance using the CIS map with "steep" stimulation sites (77%) than with the "shallow" CIS map (32%). The "steep" CIS map scores are comparable to the result obtained with the previous ACE™ map (84%).

With subject EK, no significant differences were observed, on any test measure ("steep" CIS 40%, "shallow" CIS 47%, two digit numbers 0 dB S/N). Also, comparison of the familiar ACE™ with the modified ACE™ (without the four "shallowest" electrodes) showed no significant difference in speech recognition performance (familiar ACE™ 40%, modified ACE™ 53%, monosyllables in quiet).

Figure 7:
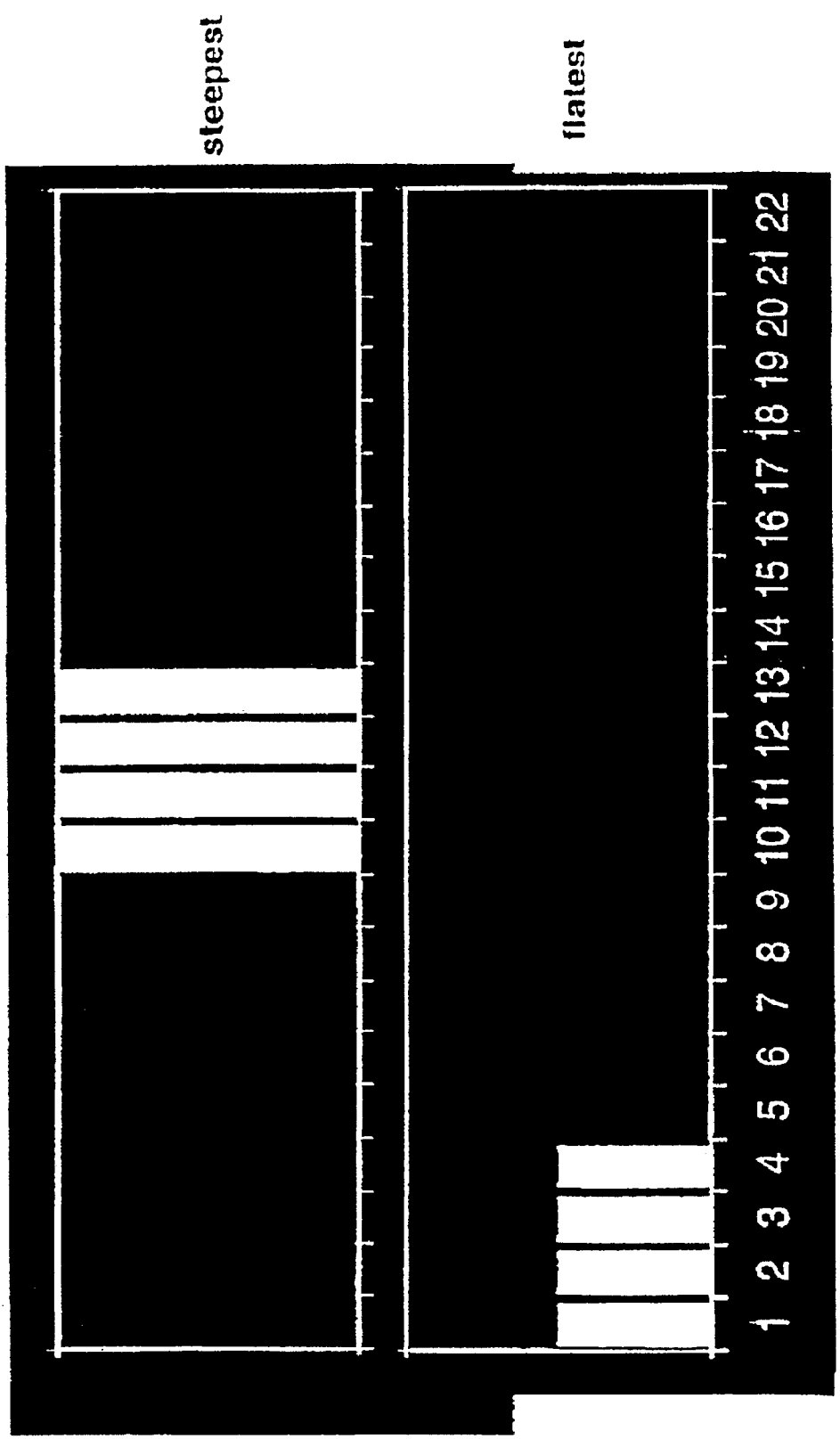
FIG. 7 shows clustering upon selection of the 4 "steepest" and "shallowest" electrodes.
Figure 8:
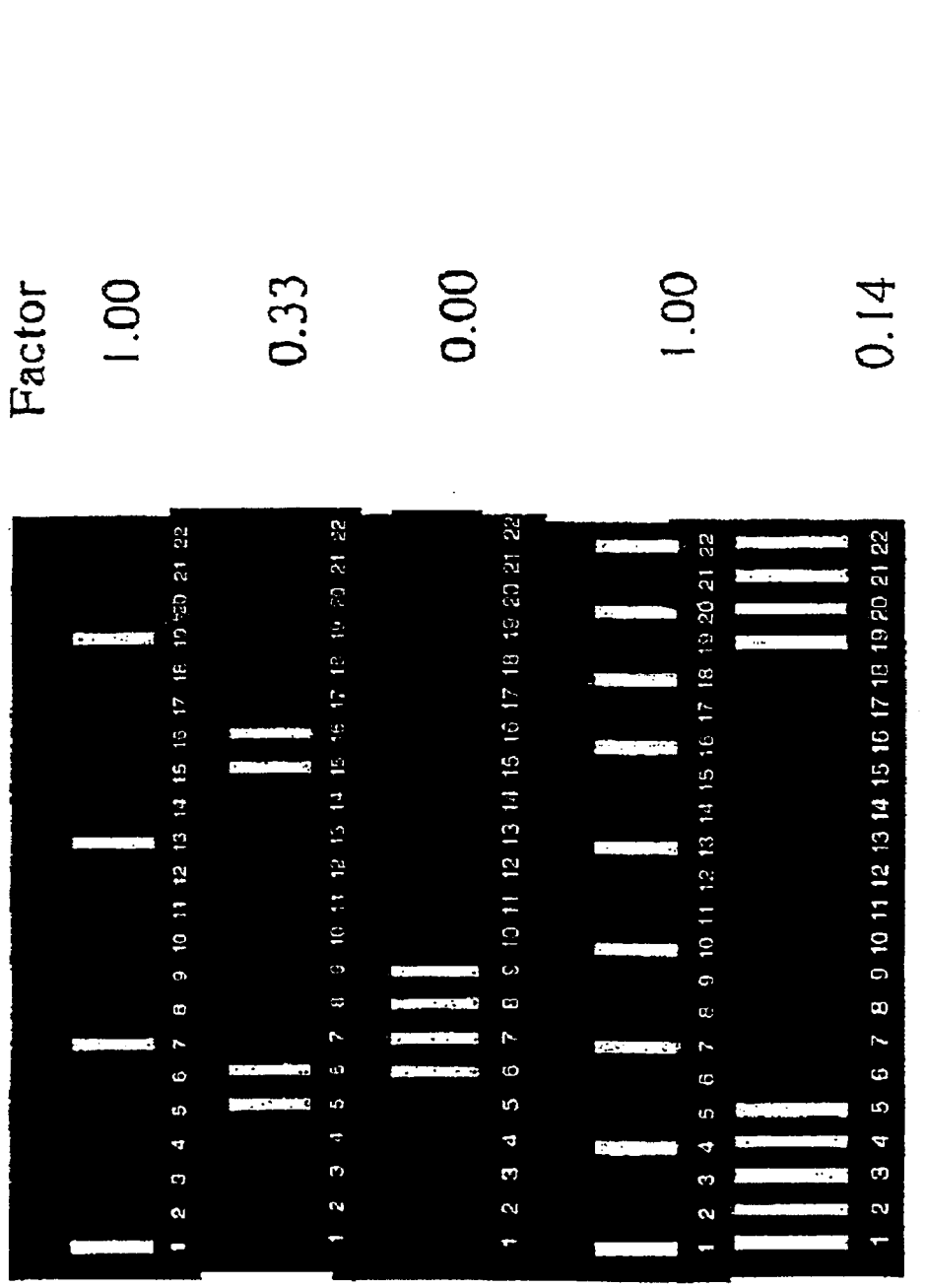
FIG. 8 shows the degree of clustering dependent on a given factor.

Selecting the four steepest/shallowest electrodes results in clustering (see FIG. 7). A trade off between uniform distribution and weighting according to slope needs to be made. A factor has been introduced which equals 1 for a perfectly equal distribution, and 0 for total clustering (see FIG. 8). Multidimensional regression analysis on a group of subjects revealed that speech perception is strongly positively correlated to this factor. Further analysis needs to be made about the distribution of the weight of the different parameters (equal distribution/slope differences) in individual subjects (showing strong slope variability vs homogeneous slope distribution).

Subject WW demonstrated remarkable improvement in speech understanding scores and sound quality when a CIS map using electrodes with steep ECAP growth function was used. In subject EK, the more uniform distribution of the ECAP amplitude growth function slope over stimulation sites might be interpreted as a fairly homogeneous distribution of surviving ganglion cell density. In this case differences In speech understanding with changing the location of stimulation sites right not be expected to the same extent, and indeed, were not demonstrated in this study. Additionally, the small number of channels (4 channels) used for the CIS maps, compared to her familiar 22-channel ACE™ map, may account for her lack of differentiation between them.

In any regard, the above example illustrates how the present invention can be implemented in a practical way and the results suggest that choosing a specific electrode set is an effective way to improve speech perception performance. Especially when using the slope of the ECAP amplitude growth function as the criterion, the speech perception score may increase considerably. Other relationships between the stimulus and the neural response to the stimulus may also be used to assist in discriminating between poor and good electrodes, as discussed above, with other relationships falling within the scope of this invention.

It will be appreciated that the example described relates to a very specific set of parameters and strategies, and that the invention is in no way limited to such aspects. Variations and additions are possible within the spirit and scope of the invention, as will be apparent to those skilled in the art.

What is claimed is:

1. In a multi-electrode neural stimulation system, a method for determining which electrodes are working well or poorly, including the steps of:
   (a) providing a series of stimuli using each electrode,
   (b) measuring the neural response to said stimuli using said electrodes, said stimuli having different stimulus levels;
   (c) calculating a value relating stimulus level to response level for each electrode; and
   (d) determining whether said electrode is working by comparing said electrode's value of step (c) with the values of step (c) for each electrode.

2. A method according to claim 1, wherein the electrodes used for measurement are one or more of the stimulating electrodes.

3. A method according to claim 1, wherein the system is an intra-cochlear prosthesis.

4. A method according to claim 3, wherein the neural response measured is the amplitude of evoked neural response.

5. A method for determining the relative responsiveness of electrodes in a multi-electrode intracochlear prosthesis, including the steps of
   (a) measuring the amplitude of the evoked response to a set of stimuli at different stimulation levels for one of the electrodes in said prosthesis;

(b) calculating a value relating the evoked responses to the stimulus levels for each electrode;

(c) repeating steps (a) and (b) for each electrode for which data is required; and (d) determining the relative responsiveness of the electrodes by comparing the values of step (b) for the tested electrodes.

6. A method according to claim 5, wherein step (b) is performed by deriving the slope of the best fit regression line on a plot of stimulus level against peak to peak amplitude of evoked response.

7. A method according to claim 6, wherein step (b) is performed by deriving the value of the peak to peak amplitude of said evoked response.

8. A method according to claim 5, wherein the relative responsiveness according to step (d) is used to construct an electrode map for selecting electrodes for stimulation.

9. A method according to claim 8, wherein the electrode map is modified in response also to the spectral distribution of the most responsive electrodes, so as to provide a more even distribution of electrodes selected for stimulation.

* * * * *